United States Patent [19]

Osborne et al.

[11] Patent Number: 5,905,092
[45] Date of Patent: May 18, 1999

[54] TOPICAL ANTIBIOTIC COMPOSITION PROVIDING OPTIMAL MOISTURE ENVIRONMENT FOR RAPID WOUND HEALING THAT REDUCES SKIN CONTRACTION

[75] Inventors: David W. Osborne; Meidong Yang, both of The Woodlands, Tex.

[73] Assignee: Virotex Corporation Reel/Frame, Fort Collins, Colo.

[21] Appl. No.: 08/796,381

[22] Filed: Feb. 6, 1997

Related U.S. Application Data

[63] Continuation-in-part of application No. 08/313,417, Sep. 27, 1994, Pat. No. 5,631,301.

[51] Int. Cl.$^6$ ............................................. A61K 47/32
[52] U.S. Cl. .................. 514/772.4; 424/445; 424/484; 424/486; 424/78.18; 424/78.02; 424/78.06; 424/78.07
[58] Field of Search ................ 514/772.4; 424/445, 424/484, 78.18, 486, 78.02, 78.06, 78.07

[56] References Cited

U.S. PATENT DOCUMENTS

| | | | |
|---|---|---|---|
| 3,328,259 | 6/1967 | Anderson | 167/84 |
| 3,579,465 | 5/1971 | Schmolka | 252/316 |
| 4,007,263 | 2/1977 | Pichierri | 424/78 |
| 4,226,232 | 10/1980 | Spence | 128/156 |
| 4,300,555 | 11/1981 | Kopito | 128/248 |
| 4,307,717 | 12/1981 | Hymes et al. | 128/156 |
| 4,326,977 | 4/1982 | Schmolka | 252/106 |
| 4,393,048 | 7/1983 | Mason, Jr. et al. | 424/132 |
| 4,430,325 | 2/1984 | Gaffar et al. | 424/128 |
| 4,474,753 | 10/1984 | Haslam et al. | 424/78 |
| 4,503,034 | 3/1985 | Maupetit et al. | 424/80 |
| 4,552,138 | 11/1985 | Hofeditz et al. | 128/156 |
| 4,554,317 | 11/1985 | Behar et al. | 525/28 |
| 4,646,730 | 3/1987 | Schonfeld et al. | 728/156 |
| 4,664,906 | 5/1987 | Sipos | 424/49 |
| 4,678,664 | 7/1987 | Schmolka | 424/65 |
| 4,678,666 | 7/1987 | Nozawa et al. | 424/81 |
| 4,728,323 | 3/1988 | Matson | 604/304 |
| 4,842,597 | 6/1989 | Brook | 604/368 |
| 4,880,416 | 11/1989 | Horiuchi et al. | 604/304 |
| 4,889,530 | 12/1989 | Smith et al. | 604/304 |
| 4,954,338 | 9/1990 | Mattox | 424/78 |
| 4,997,867 | 3/1991 | Jederstrom et al. | 524/47 |
| 5,013,769 | 5/1991 | Murray et al. | 523/111 |
| 5,061,689 | 10/1991 | Alvarez | 514/6 |
| 5,082,663 | 1/1992 | Konishi et al. | 424/445 |
| 5,126,141 | 6/1992 | Henry | 424/423 |
| 5,147,338 | 9/1992 | Lang et al. | 604/304 |
| 5,147,339 | 9/1992 | Sundstrom | 604/307 |
| 5,156,601 | 10/1992 | Lorenz et al. | 604/307 |
| 5,204,110 | 4/1993 | Cartmell et al. | 424/443 |
| 5,206,026 | 4/1993 | Sharik | 424/445 |
| 5,275,805 | 1/1994 | Nabi et al. | 424/54 |
| 5,322,689 | 6/1994 | Hughes et al. | 424/401 |
| 5,336,501 | 8/1994 | Czech et al. | 424/445 |
| 5,503,847 | 4/1996 | Queen et al. | 424/488 |
| 5,686,089 | 11/1997 | Mitra et al. | 424/405 |

FOREIGN PATENT DOCUMENTS

| | | |
|---|---|---|
| 0558423A1 | 2/1993 | European Pat. Off. . |

OTHER PUBLICATIONS

Dialog Patent and Literature Search Report, 1994.
PCT Search Report for PCT/US95/12276.

*Primary Examiner*—Thurman K. Page
*Assistant Examiner*—Lakshmi Channavajjala
*Attorney, Agent, or Firm*—Morrison & Foerster LLP

[57] ABSTRACT

A composition and method for the treatment of wounds comprising a topical semisolid composition capable of providing a moist environment for a wound and reducing skin contraction by promoting increased water content in wounds becoming dry and reduced water content in wounds having excess exudate, wherein the topical semisolid comprises water and a polyhydric alcohol having two or more gelling agents. The topical semisolid composition is used in conjunction with antibiotic formulations.

34 Claims, No Drawings

TOPICAL ANTIBIOTIC COMPOSITION PROVIDING OPTIMAL MOISTURE ENVIRONMENT FOR RAPID WOUND HEALING THAT REDUCES SKIN CONTRACTION

The present application is a continuation-in-part of U.S Pat. application Ser. No. 08/313,417 filed Sep. 27, 1994, now U.S. Pat. No. 5,631,301. The entire text of the above-referenced disclosure is specifically incorporated by reference herein without disclaimer.

BACKGROUND OF THE INVENTION

1. Field of the Invention

This invention relates to antibiotic carriers which exhibit optimal water absorption/retention properties for the promotion of wound healing and a method of treating wounds utilizing such carriers.

2. Description of the Related Art

While minor cuts, burns and abrasions seldom become infected, any break in the skin can lead to localized or even systemic infection. This is of special concern in children who may not have fully developed immune systems, or in immunocompromised individuals.

Recently, it has been shown that the amount of moisture retained in equilibrium with wounded skin, i.e., cuts, burns and abrasions, dramatically alters the healing of the wound. While an uncovered wound or loosely covered wound—exemplified by a minor cut or abrasion covered only by a flexible fabric bandage—will quickly form a hard crust or scab, this represents the least favorable environment for quick healing with minimal scarring. The only advantage of hard crust formation is that the wound tissue is thoroughly sealed from contamination by pathogens from the environment or adjacent intact skin. The disadvantage of the body's naturally evolved healing process is that fibroblasts, macrophages and other cellular repair mediators can only slowly migrate to, and function in, the wound area that is covered by dry crust. Limited mobility of fibroblast results in abnormal collagen production in the dermis which results in scarring. It is important to understand that the human body's only mechanism of infection prophylaxis, namely scabbing, results in extended time to healing of the wound and increased dermal scarring upon completion of the healing process.

The ideal environment for wound healing is a moist environment. Ideally, the moist environment should provide sufficient fluid such that the mobility of tissue repair mediators is not limited, but not so much fluid that these mediators are expelled from the tissue being repaired. It is also important that the surrounding skin not contract toward the wound as this increases the amount of scarring. As described above for an uncovered or loosely covered cut or minor abrasion, the scab results in a dry wound environment that does not have sufficient fluid to allow optimal mobilization of tissue repair mediators. Conversely, more extensive abrasions and burns, particularly after an initial hypoprofusion state, can be highly exuding wounds that are "too wet," resulting in expulsion of tissue repair mediators. Optimal therapy of these wounds requires that a significant amount of the water be removed from the wound while the tissue repair mediators remain mobile and in contact with the wounded tissue.

Thus, for optimal healing, i.e., rapid healing with minimal scarring, a controlled moist environment must be maintained such that moisture is allowed to permeate a wound which becomes too dry (i.e., dry crust or scab forming) and also allowed to escape from a wound which becomes too wet (i.e., heavily exudating), and that surrounding skin is not prompted to contract toward the wound.

While this moisture balance for a wound can be accomplished using semipermeable wound dressings, such coverings may actually hinder the healing process when placed in direct contact with the wound site. In particular, the wounded skin or repair mediators may attach to the bandage matrix resulting in introduction of a new wound upon dressing removal, or at least immobilization or removal of repair mediators. Also, semi-permeable wound dressings provide no prophylaxis against infection. As a consequence, the wound is highly prone to microbial colonization and possible infection during the healing process. Finally, wound dressings tend to be expensive, not only in terms of the cost of materials, but also in terms of the nursing time required for dressing changes.

In consideration of cost, ease of use, prophylaxis of infection, and provision of an optimal wound healing environment, the preferred treatment of wounds would be a topical semisolid containing antimicrobial actives having a broad defense against infection and being capable of maintaining a moist wound environment by promoting increased water content in wounds becoming dry and promoting reduction of water content in wounds becoming too wet. In the past, triple antibiotic topicals prepared in hydrophobic ointment vehicles have been used to provide prophylaxis against infection and promote increased water retention in wounds due to the occlusive nature of the hydrophobic ointment system. However, these products cannot promote reduction of water content in wounds which are highly exudating, because the ointment floats to the top of the exudate and is removed from the wound site. Thus, triple antibiotic topicals formulated in hydrophobic ointments are inappropriate for use on highly exudating wounds (i.e., burns and deep abrasions) because the product is quickly removed from the wound site making it ineffective both for infection prophylaxis and optimal wound healing.

Better carriers are needed for the triple antibiotic agents. Such topical semisolid compositions need to retain as much of their application weight as possible upon drying to prevent surrounding skin from contracting toward the wound.

SUMMARY OF THE INVENTION

The present invention comprises a composition and method for the treatment of wounds. The composition comprises a topical semisolid composition capable of providing a moist environment for a wound upon application by promoting increased water content in wounds becoming dry and promoting reduced water content in wounds having excess exudate, comprising vehicles, which are capable of incorporating water to at least about 30% of their initial application weight, while also being capable of retaining at least about 70% of their application weight for two hours when left at ambient conditions on a non-absorbing surface; an antibiotic formulation; and water, wherein the topical semisolid comprises a polyhydric alcohol having two or more polymeric gelling agents, selected from the group consisting of hydroxyethylcellulose, hydroxypropylcellulose, carboxymethylcellulose, polyvinylpyrrolidone, cross-linked acrylic acid polymer, PVM/MA decadiene crosspolymer and ammonium acrylates/acrylonitrogen.

DESCRIPTION OF ILLUSTRATIVE EMBODIMENTS

The present invention is directed to novel, antibiotic carrier compositions which exhibit optimal water absorption/retention properties for the promotion of wound healing with minimal scarring upon combination with antibiotic agents and methods of treating wounds using such compositions. The compositions of the present invention comprise topical semisolid carrier agents which are suitable for use in all types of wounds, particularly wounds associated with minor cuts, abrasions, and burns. The advantages of the present invention are appreciated in antibiotic applications to wound sites for prevention of infection and promotion of optimal wound healing, and are particularly effective when the semisolid carrier agents are used in combination with triple antibiotic formulations known to those skilled in the art.

The carrier compositions of the present invention comprise gel-like vehicles which are capable of incorporating water to at least 30% of their initial application weight, and when left at ambient conditions on a non-absorbing surface, retain at least 70% of their application weight for two hours. Topical preparations having these water absorption/retention properties have been proven to provide an optimal moisture environment for rapid wound healing with minimal scarring. Examples of vehicles which exhibit these water absorption/retention properties include aqueous vehicles containing propylene glycol, glycerin, or other polyhydric alcohol in conjunction with gelling agents to provide an optimal semisolid composition for wound applications.

The amount of water present in the topical semisolid compositions of the present invention is preferably at least 60% by weight, and more preferably over 70% by weight. The amount of water present is important for producing compositions that provide a moist environment for the wound.

Some preferred gelling agents include hydroxyethylcellulose (commercially available as NATROSOL® hydroxyethylcellulose produced by Aqualon), hydroxypropylcellulose (commercially available as KLUCEL® hydroxypropylcellulose produced by Aqualon), cross-linked acrylic acid polymers (such as the commercially available product CARBOPOL® cross linked acrylic acid polymer, produced by Goodrich), MVE/MA decadiene crosspolymer (such as the commercially available product STABILEZE® MVE/MA decadiene crosspolymer, produced by ISP), PVM/MA copolymer (such as the commercially available product GANTREZ® PVM/MA copolymer, produced by ISP), ammonium acrylates/acrylonitrogens (commercially available as HYPAN® ammonium acrylates/acrylonitrogens), carboxymethylcellulose and polyvinylpyrrolidone. It is preferred that the gelling agent comprise between about 0.5% to about 10% by weight of the composition. More particularly, for CARBOPOL® cross linked acrylic acid polymer the preferred compositional weight percent range is between about 2% to about 6%, while for NATROSOL® hydroxyethylcellulose or KLUCEL® hydroxypropylcellulose the preferred range is between about 0.5% to about 4%. Furthermore, the preferred compositional weight percent range for STABILEZE® PVM/MA decadiene crosspolymer and HYPAN® ammonium acrylates/acrylonitrogens is between about 1% to about 4%. The preferred compositional weight percent range for polyvinylpyrrolidone is between about 0.5% and about 10%.

Antibiotics that may be used in conjunction with the invention include: amikacin, amikacin sulfate, bacitracin, bacitracin zinc, chlortetracycline hydrochloride, dihydrostreptomycin sulfate, crystalline dihydrostreptomycin sulfate, dihydrostreptomycin hydrochloride, gentamicin sulfate, sterile gentamicin sulfate, kanamycin sulfate, sterile kanamycin sulfate, neomycin sulfate, sterile neomycin sulfate, netilmicin sulfate, oxytetracycline, paromomycin sulfate, polymyxin B, polymyxin B sulfate, sisomicin sulfate, sterile streptomycin sulfate, tetracycline hydrochloride, tobramycin and sterile tobramycin sulfate.

Typical antibiotic formulations useful in the present invention include: Silver Sulfadiazine, preferably comprising about 0.2% to about 5% by weight of the total antibiotic carrier composition; Neomycin, preferably about 0.1% to 2% by weight of the composition; Gramicidin, preferably 0.01% to 0.1% by weight; Chlortetracycline hydrochloride, preferably 1% to 5% by weight; Medocycline sulfosalicylate, preferably 0.2% to 4% by weight; Oxytetracycline, preferably 1% to 5% by weight; Tetracycline hydrochloride, preferably 0.05% to 5% by weight; about 2000 to 10,000 units of Polymyxin B; or about 200 to 1000 units of Bacitracin. The above antibiotic formulations are for illustration only, and do not represent an exhaustive list of the antibiotics that may be utilized. Those of skill in the art will recognize other antibiotic formulations that may be utilized and the typical amounts that would be useful in the present invention.

The compositions of this invention may be provided in any convenient semisolid or fluid form, such as pastes, creams, gels, aerosols, solutions or dispersions. Preferably the composition is applied to a wound via topical application of a safe and effective amount of the composition to treat the wound by any suitable means such as by manual spreading or rubbing, applicator pads, or brushes, aerosol spray, pump spray or the like. The dose range, rate and duration of treatment will vary with and depend upon the type and severity of the wound, the area of the body which is afflicted, patient response and like factors.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

To determine the degree of water absorption achieved by the carrier compositions of the present invention, approximately two grams of the vehicle was exactly weighed into a 15 mL vial. Water equivalent to 30% by weight of the vehicle (weight of vehicle x 0.3=wt of water added) was subsequently added to the vial and thoroughly mixed. The vehicle was then visually examined for indications of the extent of water incorporation. If all of the water was incorporated immediately after mixing, then the formulation was determined to be capable of incorporating moisture to at least 30% of its initial application weight.

The method of determining water retention of the compositions of the present invention was conducted by applying the water-laden carrier samples to the surface of a tared watch glass to a thickness of approximately 1–2 mm. The weight of the vehicle was then accurately determined and the vehicle-coated watch glass exposed to ambient laboratory conditions. The weight of the tared watch glass containing the vehicle was then accurately weighed after two hours, and the percent application weight after the two hour ambient exposure time was calculated according to the following formula:

[{(final weight of vehicle+tare weight watch glass)−tared weight watch glass}÷{(initial weight of vehicle+tare weight watch glass)−tared weight of watch glass}].

The following examples detail the results of the experimental tests and are provided to illustrate the water absorption/retention abilities of the compositions of the present invention.

EXAMPLE 1

30 wt% Polyethylene Glycol (PEG) 3350 and 70 wt % Polyethylene Glycol (PEG) 400 incorporated at least 30% water and retained 100% of its application weight.

EXAMPLE 2

20 wt % PEG 3350 and 80% PEG 400 incorporated at least 30% water and retained 100% of its application weight.

EXAMPLE 3

40 wt% PEG 3350 and 60% PEG 400 incorporated at 30% water and retained 100% of its application weight.

EXAMPLE 4

50 wt % PEG 3350 and 50% PEG 400 incorporated at least 30% water and retained 100% of its application weight.

EXAMPLE 5

2% CARBOPOL 980® cross linked acrylic acid polymer in water incorporated at least 30% water and retained 61% of its application weight.

EXAMPLE 6

4% CARBOPOL 980® cross linked acrylic acid polymer in water incorporated at least 30% water and retained 70% of its application weight.

EXAMPLE 7

6% CARBOPOL 980® cross linked acrylic acid polymer in water incorporated at least 30% water and retained 67% of its application weight.

EXAMPLE 8

1% HYPAN® ammonium acrylates/acrylonitrogens in water incorporated at least 30% water and retained 62% of its application weight.

EXAMPLE 9

4% HYPAN® ammonium acrylates/acrylonitrogens in water incorporated at least 30% water and retained 67% of its application weight.

EXAMPLE 10

0.5% NATROSOL® hydroxyethylcellulose in water incorporated at least 30% water and retained 64% of its application weight.

EXAMPLE 11

1% NATROSOL® hydroxyethylcellulose in water incorporated at least 30% water and retained 64% of its application weight.

EXAMPLE 12

2% NATROSOL® hydroxyethylcellulose in water incorporated at least 30% water and retained 64% of its application weight.

EXAMPLE 13

4% NATROSOL® hydroxyethylcellulose in water incorporated at least 30% water and retained 61% of its application weight.

EXAMPLE 14

1% STABILEZE® PVM/MA decadiene crosspolymer in water incorporated at least 30% water and retained 60% of its application weight.

EXAMPLE 15

2% STABILEZE® PVM/MA decadiene crosspolymer in water incorporated at least 30% water and retained 60% of its application weight.

EXAMPLE 16

4% STABILEZE® PVM/MA decadiene crosspolymer in water incorporated at least 30% water and retained 65% of its application weight.

Examples 17–19 illustrate that the use of two gelling agents causes the vehicle to retain more of its application weight, resulting in less shrinkage of the vehicle upon drying and reducing potential skin contraction toward a wound.

EXAMPLE 17

3% NATROSOL® hydroxyethylcellulose and 0.5% polyvinylpyrrolidone (PVP) in water containing 15% propylene glycol (PG) incorporated at least 30% water and retained 75% of its application weight.

EXAMPLE 18

2% NATROSOL® hydroxyethylcellulose and 2% PVP in water containing 15% PG incorporated at least 30% water and retained 74% of its application weight.

EXAMPLE 19

0.5% NATROSOL® hydroxyethylcellulose and 10% PVP in water containing 15% PG incorporated at least 30% water and retained 77% of its application weight.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition for the treatment of wounds comprising:
 a topical semisolid which is capable of providing a moist environment for a wound by promoting increased water content in wounds becoming dry and promoting reduced water content in wounds having excess exudate, comprising vehicles, which are capable of incorporating water to at least about 30% of their initial application weight, while also being capable of retaining at least about 70% of their application weight for two hours when left on a non-absorbing surface;

an antibiotic formulation;

and at least 60% by weight of water, wherein the topical semisolid comprises from about 10% to about 20% by weight of a polyhydric alcohol and from about 0.5% to about 10% by weight each of two or more gelling agents selected from the group consisting of hydroxyethylcellulose, hydroxypropylcellulose, polyvinylpyrrolidone, cross-linked acrylic acid polymer, PVM/MA decadiene crosspolymer and ammonium acrylates/acrylonitrogen.

2. The composition of claim 1 wherein the amount of water present is greater than 70% by weight.

3. The composition of claim 1 wherein one of the gelling agents is polyvinylpyrrolidone.

4. The composition of claim 1 wherein one of the gelling agents is hydroxyethylcellulose.

5. The composition of claim 1 wherein the gelling agents are hydroxyethylcellulose and polyvinylpyrrolidone.

6. The composition of claim 5 wherein the weight percent of hydroxyethylcellulose is between about 0.5% and about 6% and the weight percent of polyvinylpyrrolidone is between about 0.5% and about 10%.

7. The composition of claim 5 wherein the weight percent of hydroxyethylcellulose is between about 0.5% and about 3% and the weight percent of polyvinylpyrrolidone is between about 0.5% and about 10%.

8. The composition of claim 1 wherein the polyhydric alcohol is propylene glycol.

9. The composition of claim 1 wherein the polyhydric alcohol is glycerin.

10. The composition of claim 1 wherein the polyhydric alcohol is a blend of propylene glycol and glycerin.

11. The composition of claim 1 wherein the antibiotic formulation comprises an antibiotic selected from the group consisting of amikacin, amikacin sulfate, bacitracin, bacitracin zinc, chlortetracycline hydrochloride, dihydrostreptomycin sulfate, crystalline dihydrostreptomycin sulfate, dihydrostreptomycin hydrochloride, gentamicin sulfate, sterile gentamicin sulfate, kanamycin sulfate, sterile kanamycin sulfate, neomycin sulfate, sterile neomycin sulfate, netilmicin sulfate, oxytetracycline, paromomycin sulfate, polymyxin B, polymyxin B sulfate, sisomicin sulfate, sterile streptomycin sulfate, tetracycline hydrochloride, tobramycin, sterile tobramycin sulfate and combinations thereof.

12. A method for the treatment of wounds which comprises applying over a wound surface a composition comprising:

a topical semisolid composition which is capable of providing a moist environment for a wound by promoting increased water content in wounds becoming dry and promoting reduced water content in wounds having excess exudate, comprising vehicles, which are capable of incorporating water to at least 30% of their initial application weight, while also being capable of retaining at least 70% of their application weight for two hours when left at ambient conditions on a non-absorbing surface;

an antibiotic formulation;

and at least 60% by weight of water, wherein the topical semisolid comprises from about 10% to about 20% by weight of a polyhydric alcohol and from about 0.5% to about 10% by weight each of two or more gelling agents selected from the group consisting of hydroxyethylcellulose, hydroxypropylcellulose, polyvinyl-pyrrolidone, cross-linked acrylic acid polymer, PVM/MA decadiene crosspolymer and ammonium acrylates/acrylonitrogen.

13. The method of claim 12 wherein the semisolid composition comprises an amount of water greater than 70% by weight.

14. The method of claim 12 wherein the semisolid composition comprises polyvinylpyrrolidone as one of the gelling agents.

15. The method of claim 12 wherein the semisolid composition comprises hydroxyethylcellulose as one of the gelling agents.

16. The method of claim 12 wherein the semisolid composition comprises hydroxyethylcellulose and polyvinylpyrrolidone as the gelling agents.

17. The method of claim 16 wherein the semisolid composition comprises hydroxyethylcellulose at a weight percent of between about 0.5% and about 6%; and polyvinylpyrrolidone at a weight percent of between about 0.5% and about 10%.

18. The method of claim 16 wherein the semisolid composition comprises hydroxyethylcellulose at a weight percent of between about 0.5% and about 3% and polyvinylpyrrolidone at a weight percent of between about 0.5% and about 10%.

19. The method of claim 12 wherein the semisolid composition comprises propylene glycol as the polyhydric alcohol.

20. The method of claim 12 wherein the semisolid composition comprises glycerin as the polyhydric alcohol.

21. The method of claim 12 wherein the semisolid composition comprises a blend of propylene glycol and glycerin as the polyhydric alcohol.

22. The method of claim 12 wherein the semisolid composition comprises an antibiotic formulation comprising an antibiotic selected from the group consisting of amikacin, amikacin sulfate, bacitracin, bacitracin zinc, chlortetracycline hydrochloride, dihydrostreptomycin sulfate, crystalline dihydrostreptomycin sulfate, dihydrostreptomycin hydrochloride, gentamicin sulfate, sterile gentamicin sulfate, kanamycin sulfate, sterile kanamycin sulfate, neomycin sulfate, sterile neomycin sulfate, netilmicin sulfate, oxytetracycline, paromomycin sulfate, polymyxin B, polymyxin B sulfate, sisomicin sulfate, sterile streptomycin sulfate, tetracycline hydrochloride, tobramycin, sterile tobramycin sulfate and combinations thereof.

23. A composition for the treatment of wounds comprising:

a topical semisolid which is capable of providing a moist environment for a wound by promoting increased water content in wounds becoming dry and promoting reduced water content in wounds having excess exudate, comprising vehicles, which are capable of incorporating water to at least about 30% of their initial application weight, while also being capable of retaining at least about 70% of their application weight for two hours when left on a non-absorbing surface;

an antibiotic formulation;

and at least 60% by weight of water;

wherein the topical semisolid comprises from about 10% to about 20% by weight of propylene glycol and from about 0.5% to about 10% by weight each of hydroxyethylcellulose and polyvinylpyrrolidone.

24. The composition of claim 23 wherein the antibiotic formulation comprises a mixture of neomycin sulfate and polymyxin B sulfate.

25. The composition of claim 23, wherein the hydroxyethylcellulose comprises from about 0.5% to about 4% by weight of the composition.

26. The composition of claim 23, wherein the polyvinylpyrrolidone comprises about 2% by weight of the composition.

27. The composition of claim 23, wherein the propylene glycol comprises about 15% by weight of the composition.

28. A method for the treatment of wounds which comprises applying over a wound surface a coating of a composition comprising:
   a topical semisolid which is capable of providing a moist environment for a wound by promoting increased water content in wounds becoming dry and promoting reduced water content in wounds having excess exudate, comprising vehicles, which are capable of incorporating water to at least 30% of their initial application weight, while also being capable of retaining at least 70% of their application weight for two hours when left at ambient conditions on a non-absorbing surface;
   an antibiotic formulation;
   and at least 60% by weight of water,
   wherein the topical semisolid comprises from about 10% to about 20% by weight of propylene glycol and from about 0.5% to about 10% by weight each of hydroxyethylcellulose and polyvinylpyrrolidone.

29. The method of claim 27, wherein the antibiotic formulation comprises a mixture of neomycin sulfate and polymyxin B sulfate.

30. The composition of claim 27, wherein the hydroxyethylcellulose comprises from about 0.5% to about 4% by weight of the composition.

31. The composition of claim 27, wherein the polyvinylpyrrolidone comprises about 2% by weight of the composition.

32. The method of claim 27, wherein the propylene glycol comprises about 15% by weight of the composition.

33. A composition for the treatment of wounds comprising:
   a topical semisolid which is capable of providing a moist environment for a wound by promoting increased water content in wounds becoming dry and promoting reduced water content in wounds having excess exudate, comprising vehicles, which are capable of incorporating water to at least about 30% of their initial application weight, while also being capable of retaining at least about 70% of their application weight for two hours when left on a non-absorbing surface;
   an antibiotic formulation;
   and at least about 70% by weight of water;
   wherein the topical semisolid comprises from about 10% to about 20% by weight of a polyhydric alcohol and from about 0.5% to about 10% by weight each of two or more gelling agents selected from the group consisting of hydroxyethylcellulose, hydroxypropylcellulose, carboxymethylcellulose, polyvinylpyrrolidone, cross-linked acrylic acid polymer, PVM/MA decadiene crosspolymer and ammonium acrylates/acrylonitrogen.

34. A method for the treatment of wounds which comprises applying over a wound surface a composition comprising:
   a topical semisolid composition which is capable of providing a moist environment for a wound by promoting increased water content in wounds becoming dry and promoting reduced water content in wounds having excess exudate, comprising vehicles, which are capable of incorporating water to at least 30% of their initial application weight, while also being capable of retaining at least 70% of their application weight for two hours when left at ambient conditions on a non-absorbing surface;
   an antibiotic formulation;
   and at least about 70% by weight of water,
   wherein the topical semisolid comprises from about 10% to about 20% by weight of a polyhydric alcohol and from about 0.5% to about 10% by weight each of two or more gelling agents selected from the group consisting of hydroxyethylcellulose, hydroxypropylcellulose, carboxymethylcellulose, polyvinyl-pyrrolidone, cross-linked acrylic acid polymer, PVM/MA decadiene crosspolymer and ammonium acrylates/acrylonitrogen.

* * * * *